(12) United States Patent
Matusch (10) Patent No.: US 8,529,499 B2
(45) Date of Patent: *Sep. 10, 2013

(54) DISPOSABLE INJECTOR WITH AT LEAST ONE CENTRAL TRACTION ROD

(75) Inventor: Rudolf Matusch, Marburg (DE)

(73) Assignee: LTS Lohmann Therapie-Systeme AG, Andernach (DE)

( * ) Notice: Subject to any disclaimer, the term of this patent is extended or adjusted under 35 U.S.C. 154(b) by 367 days.

This patent is subject to a terminal disclaimer.

(21) Appl. No.: 12/460,382

(22) Filed: Jul. 17, 2009

(65) Prior Publication Data

US 2009/0281496 A1 Nov. 12, 2009

Related U.S. Application Data

(63) Continuation-in-part of application No. PCT/EP2008/000319, filed on Jan. 17, 2008.

(30) Foreign Application Priority Data

Feb. 16, 2007 (DE) .......................... 10 2007 008 369

(51) Int. Cl.
*A61M 5/30* (2006.01)
*A61M 5/20* (2006.01)

(52) U.S. Cl.
USPC .......................................... 604/68; 604/135

(58) Field of Classification Search
USPC ................... 604/68, 134, 135, 136, 137, 138, 604/139, 131, 218, 228, 229
See application file for complete search history.

(56) References Cited

U.S. PATENT DOCUMENTS

| | | | | |
|---|---|---|---|---|
| 2,762,369 A | * | 9/1956 | Venditty | 604/68 |
| 2,762,370 A | * | 9/1956 | Venditty | 604/68 |
| 3,853,125 A | * | 12/1974 | Clark et al. | 604/70 |
| 4,316,463 A | * | 2/1982 | Schmitz et al. | 604/135 |
| 4,553,962 A | | 11/1985 | Brunet | |
| 4,565,543 A | * | 1/1986 | Bekkering et al. | 604/135 |
| 4,874,367 A | | 10/1989 | Edwards | |
| 4,968,302 A | * | 11/1990 | Schluter et al. | 604/135 |
| 6,224,568 B1 | * | 5/2001 | Morimoto et al. | 604/89 |
| 2004/0039336 A1 | | 2/2004 | Amark et al. | |
| 2005/0124940 A1 | | 6/2005 | Martin et al. | |
| 2005/0165349 A1 | * | 7/2005 | Stamp | 604/70 |
| 2006/0224124 A1 | | 10/2006 | Scherer | |
| 2007/0017532 A1 | | 1/2007 | Wyrick | |
| 2007/0073232 A1 | | 3/2007 | Pickhard | |

FOREIGN PATENT DOCUMENTS

| | | |
|---|---|---|
| CA | 2 356 614 A1 | 4/2000 |
| DE | 0 144 625 A | 6/1985 |
| FR | 393 189 A | 12/1908 |
| WO | WO 95/03844 | 2/1995 |

* cited by examiner

*Primary Examiner* — Laura Bouchelle
*Assistant Examiner* — Jenna Zhang
(74) *Attorney, Agent, or Firm* — R. S. Lombard; K. Bach

(57) ABSTRACT

A disposable injector having a housing (10) in which are arranged at least one mechanical spring energy reservoir (50), at least one cylinder-piston unit (100) that can be filled at least in part with an active substance, at least one piston actuation plunger (60) and at least one trigger unit (80). The spring energy accumulator plunger (60) has at least one tension bar (61) with at least one support surface (63) at the upper end thereof. Locking elements (16) supported on the housing lie on the support surface(s) and are secured in the locking position by a triggering element (82) placed in a locking position (8). The triggering element has a release position (9) that causes the locking element (16) to be unlocked for release of the active substance.

9 Claims, 7 Drawing Sheets

DISPOSABLE INJECTOR WITH AT LEAST ONE CENTRAL TRACTION ROD

CROSS-REFERENCE TO RELATED APPLICATION

This is a continuation-in-part application of pending international application PCT/EP 2008/000319 filed Jan. 17, 2008 and claiming the priority of German Application No. 10 2007 008 369.8 filed Feb. 16, 2007.

BACKGROUND OF THE INVENTION

The invention relates to a disposable injector with a housing in which or on which—in each case at least in some regions—at least one mechanical spring energy reservoir, at least one cylinder/piston unit—which can be filled at least temporarily with active substance, at least one piston—actuating ram and at least one triggering unit are arranged, wherein the spring energy reservoir comprises at least one pretensioned spring element, and wherein at least part of the piston-actuating ram is positioned between the spring energy reservoir and the piston of the cylinder/piston unit.

An injector of this type, inter alia, is known from EP 0 595 508 B1. It has a spring-pretensioned piston, the rear piston rod of which has an elastic region with a throat at its free end. In the region of the throat, the piston is clamped firmly to the injector housing in a frictional and interlocking manner. For this purpose, a triggering pin is inserted in the free end of the piston rod, the triggering pin keeping the throat and the border regions thereof at their maximum diameter. Displacement of the triggering pin enables the diameter of the piston-rod end region to be reduced by the clamping forces in effect, and therefore the clamping effect of the piston rod in relation to the housing is lost. As a result, the spring pretensioned piston moves.

Therefore, the object of the present invention is that of developing a disposable injector of modular design which, with a small overall size, has only a small number of components and, while being easy to handle, ensures safe storage and reliable operation.

SUMMARY OF THE INVENTION

The present invention provides a disposable injector having a housing (10) in which are arranged at least one mechanical spring energy reservoir (50), at least one cylinder-piston unit (100) that can be filled at least in part with an active substance such as a medicament, at least one piston actuation ram (60) in operative arrangement with the spring energy reservoir (50) and at least one trigger unit (80). The spring-loaded piston actuation ram (60) has at least one tension bar (61) with at least one support surface (63) at the rear end thereof. Locking elements (16) supported on the housing (10) at support surface(s) of the housing and are secured in the locking position by a triggering element (82) placed in a locking position (8). The triggering element has a release position (9) that causes the locking element (16) to be unlocked.

For this purpose, the spring-loaded piston actuation ram (60) has the at least one central tension or traction bar (61) with at least one supporting surface (63) in the region of its upper or rear end. Locking elements (16) which are supported on the housing bear against the supporting surface (63) or the supporting surfaces (63), the locking position (8) of the locking elements (16) is secured by the trigger unit (80) positioned in a locking position. The trigger unit (80) has a release position (9) which causes the locking elements (16) to be released.

With the invention, for example, a needle-free disposable injector is provided, the piston actuation ram (60) is released upon a triggering operation of the disposable injector. For this purpose, in order to pretension and retain the spring energy reservoir (50), at least part of the piston actuation ram (60) bears with at least one surround-like contour at least frictionally against the housing (10) or a component arranged on the housing, for example a locking element (16). The locking elements (16) are retained in their locking position by the trigger unit (80) until the disposable injector is used. In order to trigger the injector, the locking elements (16) are released, and therefore the piston actuation ram (60) can move parallel to the centre line of the disposable injector—under the action of the spring energy reservoir (50).

BRIEF DESCRIPTION OF THE DRAWINGS

Further details of the invention are disclosed from the following schematically illustrated exemplary embodiments, in which.

DETAILED DESCRIPTION OF THE PARTICULAR EMBODIMENTS

Figure 1:
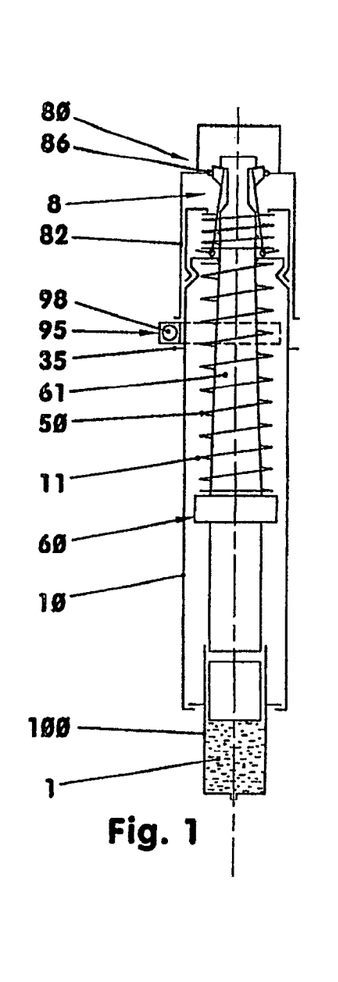
FIG. 1 shows a disposable injector with a central piston actuation ram (60)
Figure 2:
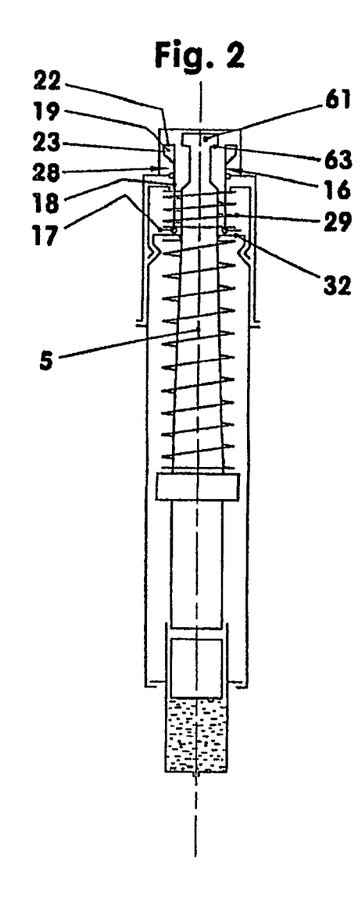
FIG. 2 is as per FIG. 1, but released and actuated.
Figure 3:
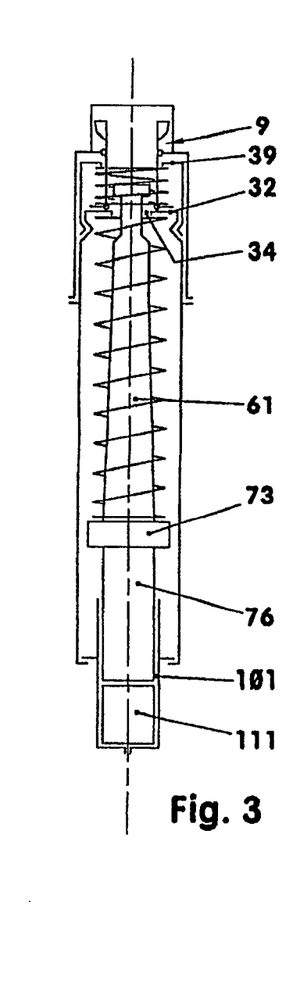
FIG. 3 is as per FIG. 2, but after the ejection of medicament.

FIGS. 1 to 3 show the simplified principle of a disposable injector with a permanently charged spring energy accumulator or reservoir (50). The disposable injector comprises a housing (10), a, for example, filled cylinder/piston unit (100), a piston-actuating ram (60) with a tension bar (61) and a helical compression spring (50) as the spring energy accumulator or reservoir. In addition, a triggering element (82) and a securing element (95) are operatively arranged on the housing (10).

The housing (10) is a cup-shaped hollow body which is open at the bottom and has an elevated intermediate base (32). The intermediate base (32) has, for example, a central opening (34) through which, according to FIG. 1, the tension bar (61) is inserted. The tension bar (61) bears with at least one supporting surface (63) against locking elements (16) which are mounted on the intermediate base (32), for example on both sides of the tension bar (61), see FIG. 2. The tension bar (61) is not transversely moveable, but is axially moveable during operation of the injector.

According to FIGS. 1 to 3, the locking elements (16) are special angle levers which are mounted in the region of their buckling point on the intermediate base (32) in an articulated manner. Each locking element (16) has a short lever arm (17) and a long lever arm (18). At the upper end, the long lever arm (18) has a supporting element (19) with an upper bearing surface (22) and a lateral bearing surface (23). An offset contour (28) is located below the laterally projecting supporting element (19). The distance of said offset contour from the centre line (5) is considerably shorter than the shortest distance between the lateral bearing surface (23) and the centre line (5).

The locking elements (16) may be fastened, if appropriate, to a ring-like component. Said component then rests, for example, on the intermediate base (32). The locking elements (16) protrude upward from it. Those sections of the ring-like component which are placed between two locking elements in each case serve, inter alia, as a torsion spring which brings the locking elements (16) from a locking position (8) into a release position (9).

The upper bearing surface (22) of the individual locking element (16) makes contact with the supporting surface (63) of the tension bar (61). In the locking position (8), the bearing surface (22) and the supporting surface (63) each adopt at least approximately the same angle in relation to the centre line (5). Said angle lies, for example, within a range of from 10 to 85 degrees of angle, with the higher degrees of angle being preferred here.

The upper bearing surfaces (22) and the supporting surfaces (63) are generally curved spherically and matched at least approximately to one another in the locking position (8). However, surfaces (22) and (63) of planar or flat design are also conceivable.

The shorter lever (17) of the individual locking element (16) protrudes laterally from the long lever (18). In the exemplary embodiment, see FIGS. 2 and 3, the short lever (17) is oriented radially with respect to the centre line (5). A helical compression spring (29) rests on the short lever (17) of all of the locking elements (16). The helical compression spring (29) is upwardly supported on a housing surround (39). The helical compression spring (29) causes the locking elements (16) to be pivoted apart. In the process, according to FIG. 1, the lateral bearing surfaces (23) of the locking elements (16) are in each case pressed against the triggering element (82).

The triggering element (82) is a type of cap-shaped pushbutton which is placed onto the upper end of the housing (10) in a longitudinally displaceable manner. For this purpose, it bears, mounted in a sliding manner, against the outer surface of the housing (10) which outer surface is, for example, in the shape of a cylindrical casing.

Supporting webs (86) protrude, for example radially inwards, from the inside of the triggering element (82). The supporting webs (86), which may also be part of a ring or of a perforated disc, have front edges against which the lateral supporting surfaces (23) of the locking elements (16) are supported.

The manner in which the triggering is carried out is not restricted to the variant described here. Instead of the longitudinally displaceable triggering element (82) acting on the locking elements (16), use may be made, for example, inter alia of an eccentric mechanism, a helical mechanism or a lever mechanism.

Figure 4:
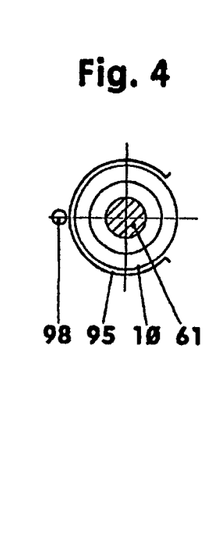
FIG. 4 shows a cross section for FIG. 1 in the region of the securing element.

According to FIG. 1, the triggering element (82) bears against a securing element (95). The latter is downwardly supported, for example, against a housing collar (35). The securing element (95) is, for example, an elastic, omega-shaped clip which resiliently surrounds the outer surface of the housing (10) at an angle of approximately 120 degrees of angle. According to FIGS. 1 and 4, it has a handle (98) on the left side via which it can be pulled off laterally—for release purposes.

The piston-actuating ram (60) is arranged in the housing (10). It is divided into three regions. The lower region is the piston slide (76). Its diameter is somewhat smaller than the inside diameter of the cylinder (101) of the cylinder/piston unit (100). The lower end surface of the piston slide (76) acts directly on the piston (111).

Of course, the piston slide (76) may also be designed as a separate component. Moreover, it is then guided on the inner wall of the housing (10).

The central region is the ram plate (73). The ram plate (73) is a flat and at least in some regions cylindrical disc, the outside diameter of which is a few tenths of a millimeter smaller than the inside diameter of the housing (10) in the casing region (31). The upper region is the tension bar (61).

The cylinder/piston unit (100) is fastened in the lower part of the housing (10). The cylinder/piston unit (100) here comprises a cylinder (101) which is filled with an injection solution (1) and in which a piston (111) sits in the rear or upper position. Above the piston (111), the piston-actuating ram (60) is arranged in the housing (10), for example in such a manner that, although it does not touch the piston, it is guided laterally by means of its lower end in the upper region of the cylinder (101).

The helical compression spring (50) sits in a pretensioned manner between the ram plate (73) and the elevated base (32) of the housing (10).

In order to actuate the disposable injector, first of all the securing element (95) is pulled off laterally, the nozzle bore (106) of the disposable injector is positioned on the injection location and, subsequently, the triggering element (82) is pressed, for example by one finger of the hand carrying the disposable injector. In the process, the supporting webs (86) of the triggering element (82) slide along the lateral bearing surfaces (23) of the locking elements (16) until they enter the region of the offset contour (82). When the supporting webs (82) have reached the offset contour (28), they spring back under the action of the helical compression spring (29), i.e. the locking elements (16) pivot outwards, that is away from the centre line (5).

Said pivoting-away action is assisted by the bearing conditions in the region of the supporting surface (63) and the upper bearing surface (22). Because of the spatial inclination of said surfaces (22, 63), the spring energy reservoir (50) causes transverse forces to act permanently on the locking elements (16), the transverse forces pressing the latter outwards.

By the locking elements (16) pivoting away, the tension bar (61) is released. It can now shoot downwards through the bore (34) without obstruction.

FIGS. 5 to 10 show an embodiment of the principle described in FIGS. 1 to 4. The supporting component here is the housing (10). It has a largely tubular design and is divided into three functional regions (15, 31, 41). According to FIGS. 5 and 6, the upper region is the triggering region (15). It is adjoined by the casing region (31). An elevated base (32) is arranged between the two regions. The elevated base (32) has a central recess (34).

Figures 5, 6:
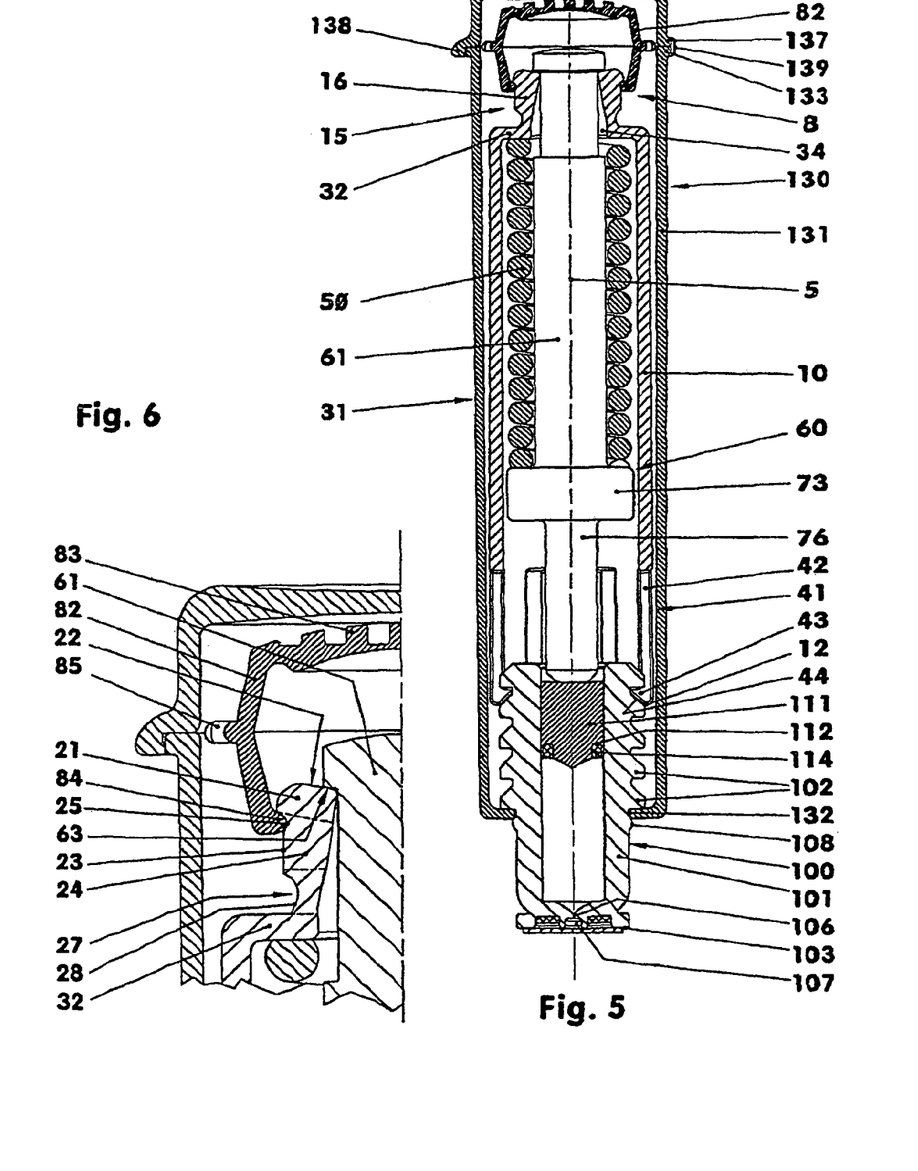
FIG. 5 shows a disposable injector with a piston actuation ram (60) which has a supporting surface which is in the shape of a conical casing or is wedge-shaped.
FIG. 6 shows an enlargement of a detail of FIG. 5.
Figure 9:
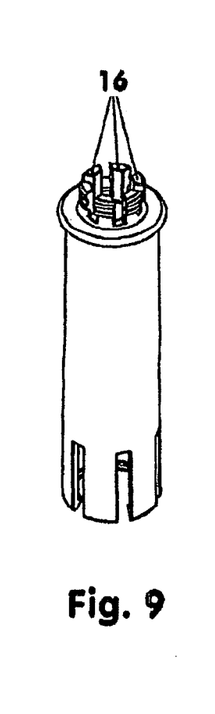
FIG. 9 shows a perspective plan view of the housing of the disposable injector according to FIG. 5.

In the triggering region (15) of the housing (10), for example, six integrally locking or flexurally elastic elements (16) are arranged on the upper side of the elevated base (32), the flexurally elastic elements (16) are monolithic portions of the elevated base (32) and extend therefrom, see also the perspective view according to FIG. 9. FIG. 5 illustrates two mutually opposite locking or flexurally elastic elements (16) in longitudinal section. The individual locking or flexurally elastic element (16) is divided into three regions. The first region is the bearing region (21), see FIG. 6. The latter makes contact, by means of the bearing surface (22), with the supporting surface (63) of the tension bar (61). At the same time, its upper inner edge bears, if appropriate, against the stem of the tension bar (61), which is cylindrical here and is reduced in size—below the supporting surface (63). If appropriate, the locking elements (16) have ceramic armouring at least in the region of the bearing surfaces (22).

The second region is the retaining region (24) of the locking elements (16). It is separated from the bearing region (21) by a notch (25). The lower supporting border (84) of a triggering element (82) bears in the notch (25) in a manner secure against slipping in the locking position (8). The lateral bearing surface (23) which also includes the notch (25) is located below the notch (25).

The individual locking element (16) is connected to the housing (10) via the third region, the "offset region" (27). The offset region (27) has an offset notch (28). The border (84) of the triggering element (82) projects into said offset notch in the release position (9), see FIGS. 7 and 8.

The fixing region (41) for receiving the insertable cylinder/piston unit (100) is located in the lower region of the housing (10). The fixing region (41) comprises, for example, six spring hooks (42) which each end in an inwardly directed hook tip (43). Towards the lower housing end side (12), the hook tips (43) have a beveled portion (44) extending over the entire thickness of the hook. The length and the spring rate of the spring hooks (42) are dimensioned in such a manner that the internal components (50, 100) required for the operation of the disposable injector can be installed without plastic deformation of the spring hooks (42).

One of said internal components is the cylinder/piston unit (100), of FIG. 5. It comprises a cylinder (101) and a piston (111). The cylinder (101) is a cup, for example a thick-walled cup, the, if appropriate cylindrical, outer wall of which bears, for example, five encircling latching ribs (102). The sum of the latching ribs (102) has, for example, a serrated profile in cross section, with the division between the tooth-like latching ribs (102) being equidistant. The maximum diameter of the latching ribs (102) is slightly smaller than the inside diameter of the housing (10) in the fixing region (41). The diameter of the regions located between adjacent latching ribs (102) corresponds to the minimum diameter of the housing (10) in the region of the hook tips (43).

A rod-free piston (111) sits in the, for example, cylindrical bore of the cylinder (101). On its front end surface, which is of approximately conical design, the piston (111) has an axial annular groove (112) for receiving a sealing ring (114) or a permanently elastic sealing compound. If appropriate, a, for example cylindrical, metal plate (116) is embedded in the rear end surface of the piston (111), see FIG. 11.

In the centre of the bore of the cylinder 101, the cylinder base of which is at least approximately matched to the contour of the front or bottom piston end side, there is a short cylindrical nozzle-like bore (106).

The diameter of the short cylindrical nozzle-like bore (106) is approximately 0.1 to 0.5 millimeter. Said bore (106) is one to five times as long as its diameter. It opens into a cylindrical recess (107) of the base-side, outer end surface (103) of the cylinder (101).

The spring energy reservoir (50) or the driving unit of the disposable injector is arranged between the piston (111) and the triggering region (15). The spring energy reservoir (50) is a helical compression spring which is arranged on a piston-actuating ram (60) with a tension bar (61). The piston-actuating ram (60), which is subjected to a spring-force loading, is supported by means of the tension bar (61) with the locking elements (16) of the housing (10).

The piston-actuating ram (60) is likewise divided into three regions. The lower region is the piston slide (76), the central region is the ram plate (73) which supports the spring element (50), and the upper region is the tension bar (61), see also the description for FIGS. 1 to 4.

The cap-shaped, push-button-like triggering element (82), see FIGS. 5 and 6, sits in the triggering region (15) in its upper locking position (8). The triggering element (82) has a base (83) which is grooved on the outside, an inwardly curved border (84) and an encircling outer border (85) which protrudes in a partially interrupted manner. In the locking position (8), the border (84) sits in the notches (25) of the locking elements (16).

Figure 10:
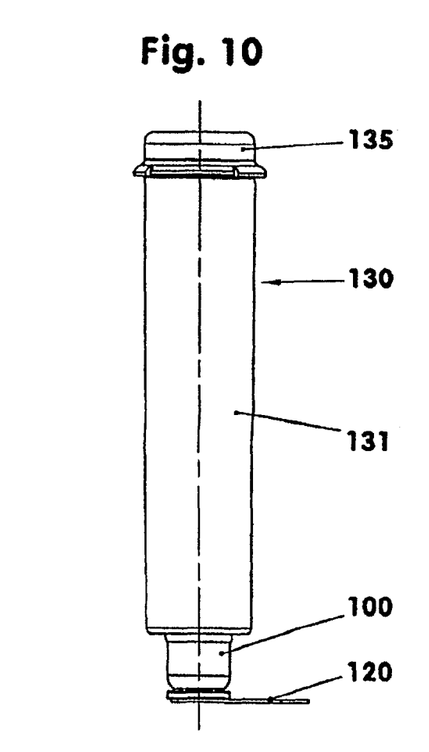
FIG. 10 shows a side view of the disposable injector according to FIG. 5, but before use.

The outer border (85) serves as a guide aid in relation to a surrounding housing (130), see also FIG. 10. A surrounding housing (130) of this type comprises a lower part (131) and an upper part (135). According to FIG. 5, the lower part (131), which, for example, is larger, surrounds the entire housing (10) and part of the cylinder/piston unit (100). The lower-part base has a bore (132) through which the cylinder/piston unit (100) projects downwards. The lower part (131) is fixed here between the lowermost latching rib (102) and an encircling elevation (108).

At the top, the lower part (131) ends, see FIG. 5, in a widened, flange-like border (133). The upper part (135) rests on said border (133) by means of its, for example, likewise flange-like border (137). A surround (138) and a film hinge (139), for example, are arranged on said border (137). The film hinge (139) connects the parts (131) and (135) as a single part. The surround fixes the upper part (135) on the lower part (131) by engaging elastically around the border (133). The upper part (135) can be swung away from the lower part (131) by hand with little effort.

Without the film hinge (139), the lower part (131) is a component which is rotationally symmetrical with respect to the centre line (5). The upper part (135) can be fastened to it, for example also by means of a screw or bayonet fastening. A seal may also be arranged between the upper part (135) and the lower part (131) or may be integrally formed, for example, on one of the parts (131, 135).

The completely closed surrounding housing (130), the lower part (131) of which, if appropriate, is additionally sealed in relation to the cylinder/piston unit (100) by means of a seal, protects the disposable injector in a simple and secure manner. It therefore serves at the same time as a securing element.

Figure 7:
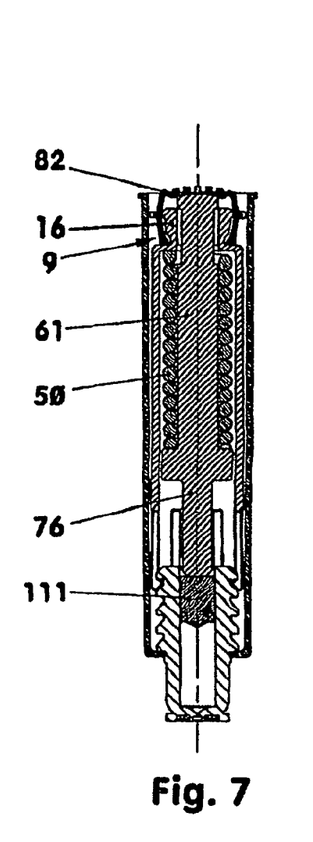
FIG. 7 is as per FIG. 5, but released and actuated.
Figure 8:
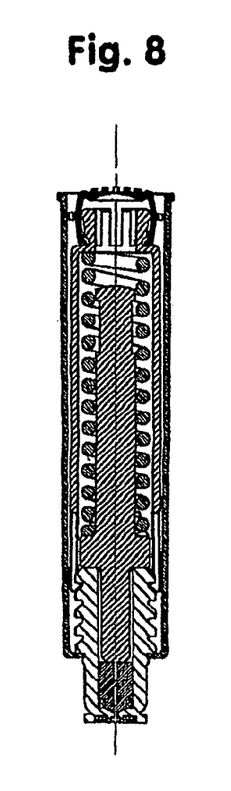
FIG. 8 is as per FIG. 5, but after the ejection of medicament.

FIG. 7 shows the disposable injector without the upper part (135), i.e. released, with the triggering element (82) pressed downwards. As the triggering element (82) is pressed downwards, the locking elements (16) are released from the tension bar (61) inter alia by springing back elastically and/or being pressed away plastically. The tension bar (61) can now shoot downwards under the action of the spring element (50) and displace the piston (111) by means of the piston slide (76), see FIG. 8.

FIG. 10 shows the disposable injector, which is still unactuated, in the commercially available state. The housing (10), not visible here, and the triggering element (82) are surrounded in a protected manner by the surrounding housing (130). The lower end side of the cylinder/piston unit (100) is closed in a sterile manner with the aid of an adhesive seal (120) which can be torn off.

FIGS. 11 to 15 illustrate a variant of the disposable injector, the tension bar (61) which is, for example, for the most part cylindrical, bears over a large surface area in a frictional manner against, for example, four locking elements (16).

The housing (10) here too is essentially a smooth tube with an elevated, planar base (32) which, in addition, protrudes radially slightly above the casing region (31). A central bore (34) is incorporated in the base (32) for the passage of the piston-actuating ram (60). Particularly elastic locking elements (16) are arranged around the bore. The number of locking elements (16) is usually between 3 and 12.

Figure 11:
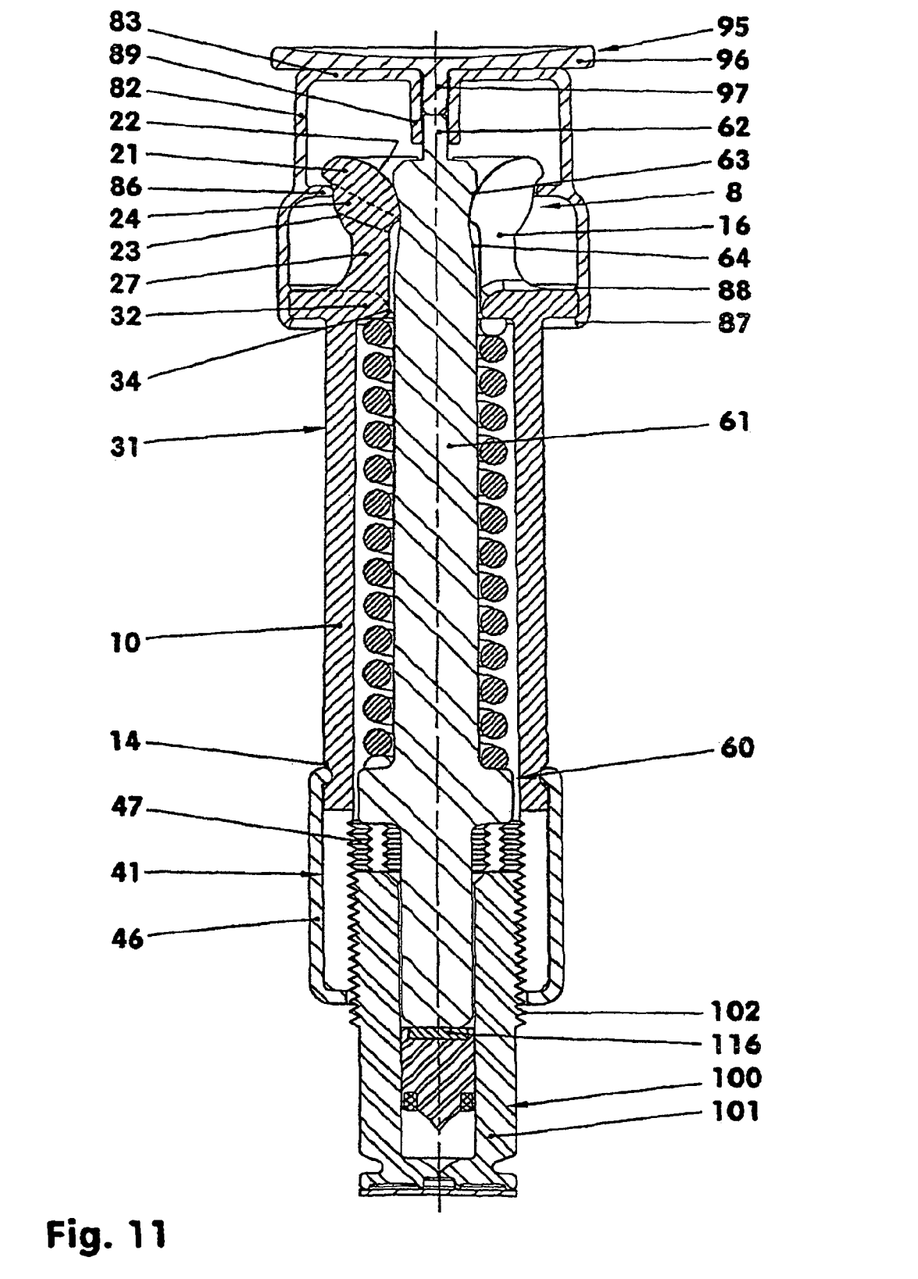
FIG. 11 shows a disposable injector with a tension bar (61) which has a supporting surface in the shape of a toroidal partial casing.
Figure 12:
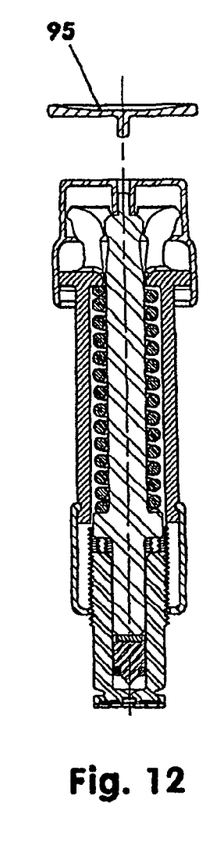
FIG. 12 is as per FIG. 11, but released and actuated.
Figure 13:
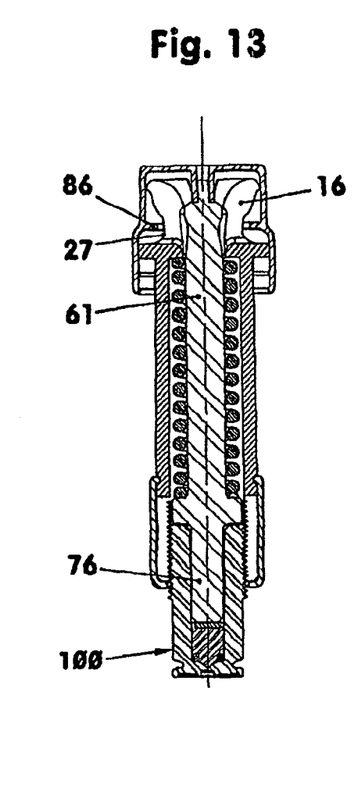
FIG. 13 is as per FIG. 11, but after the ejection of medicament.
Figure 14:
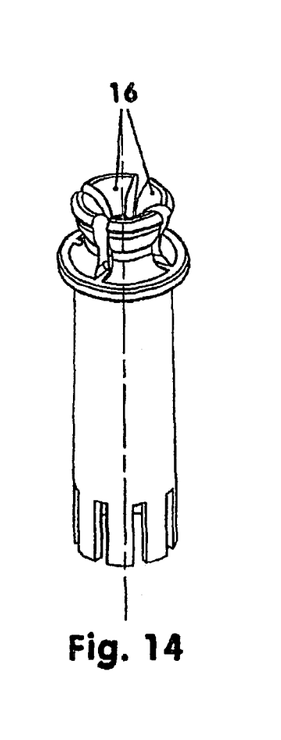
FIG. 14 shows a perspective plan view of the housing of the disposable injector according to FIG. 11.

The individual locking element (16), one of which is illustrated specifically in section on the left side of FIG. 11, has—as viewed in cross section—a bearing surface (22) with a continuously curved contour in the bearing region (21). The contour is part of a toroidal outer surface, see also FIG. 14.

The tension bar (61) has a throat-like constriction which, in some regions, constitutes the supporting surface (63) on the tension-bar side. Said supporting surface is part of a toroidal inner surface. The latter has, at least approximately, the same circular cross-sectional radius and the same annular radii as the toroidal outer surface of the bearing surface (22). This results in particularly large contact surfaces between the tension bar (61) and the locking elements (16). In this case, the supporting surface (63) reaches as far as the narrowest point of the constriction.

Below said supporting surface (63), the tension bar (61) has, for example, a rotationally symmetrical transition surface (64) which connects the supporting surface (63) to the remaining cylindrical outer surface of the tension bar (61). The transition surface (64) and the supporting surface (63) have exclusively continuous transitions. The other surface transitions do not have any sharp-edged steps either, and therefore, even in the case of a small tension-bar diameter, because of low stress concentrations a large tensile force can be permanently supported.

The retaining region (24) of the locking elements (16) is the region in which the triggering element (82) bears by means of its supporting web (86).

For this purpose, the triggering element (82) is designed as a cap sitting on the housing (10). In the locking position (8), the triggering element (82) engages around the protruding housing base (32). For this purpose, it has an engaging-around border (87) and an encircling web (88).

The supporting web (86) is located in the central region of the cap. At the top, the cap (82) has a base (83) with a tube section (89) embedded in it.

A securing element (95) which comprises a plate-like disc (96) and an integrally formed locking pin (97) rests on the cap (82). The locking pin (97) is inserted in a centred manner in the tube section (89) of the cap (82). At the same time, the locking pin (97) bears against a central guide pin (62) of the tension bar (61). In the locking position (8), the guide pin (62) is inserted, at least in some regions, in the tube section (89) of the cap (82).

The retaining region (24) of the locking elements (16) is located below the supporting web (86) of a triggering element (82) positioned in the locking position (8). The contour of the retaining region (24) is part of a torus, the centre point of which lies on the centre line (5) level with the supporting web (86).

In the locking position (8), the offset region (27) which adjoins the retaining region (24) has an outside diameter which is approximately 20 to 25% smaller than the largest outside diameter of the retaining region (24).

The four locking elements (16) of this variant have large supporting cross sections in the retaining region (24). In the offset region (27), the sum of the four cross-sectional surfaces is 60 to 70% of the overall cross-sectional surface of the housing (10) below the base (32).

The lower region of the casing section (31) has an elastic fixing region (41) for the mounting of a cylinder/piston unit (100). It has an internal grooved profile (47) which is interrupted a number of times by longitudinal slots. The cylinder/piston unit (100) is retained by means of the grooved profile (47), the unit having, at least in some regions, a corresponding external grooved profile (102). By means of the profile (47, 102) which is oriented transversely with respect to the centre line (5), the cylinder/piston unit (100) can be positioned in various latching positions in the housing (10) for the purpose of varying the cylinder volume. Two adjacent latching positions differ by a difference in cylinder volume of 0.025 ml. The individual grooves each have a toothed cross section as are to be found, for example, in the case of steel conduit threads or British Standard Whitworth threads. However, the toothed cross sections may also be undertaken by trapezoidal threads, buttress threads or pipe threads.

After the insertion of the cylinder/piston unit (100), a clamping sleeve (46) which secures the position of the unit (100) is pushed over the fixing region (41). For this purpose, the clamping sleeve (46) latches in an annular groove (14) of the housing (10).

Figure 15:
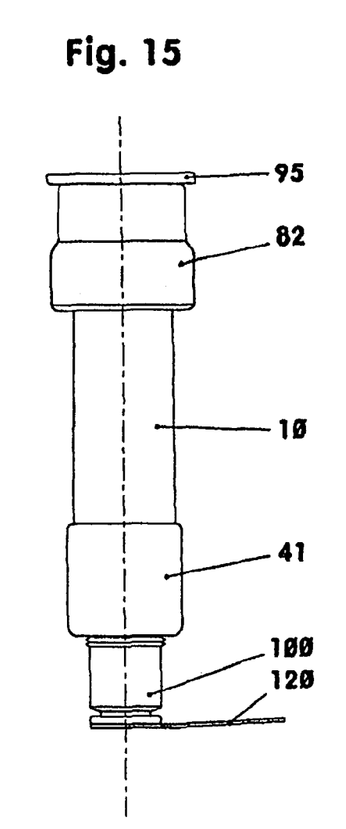
FIG. 15 shows a side view of the disposable injector according to FIG. 11, but before use.
Figure 16:
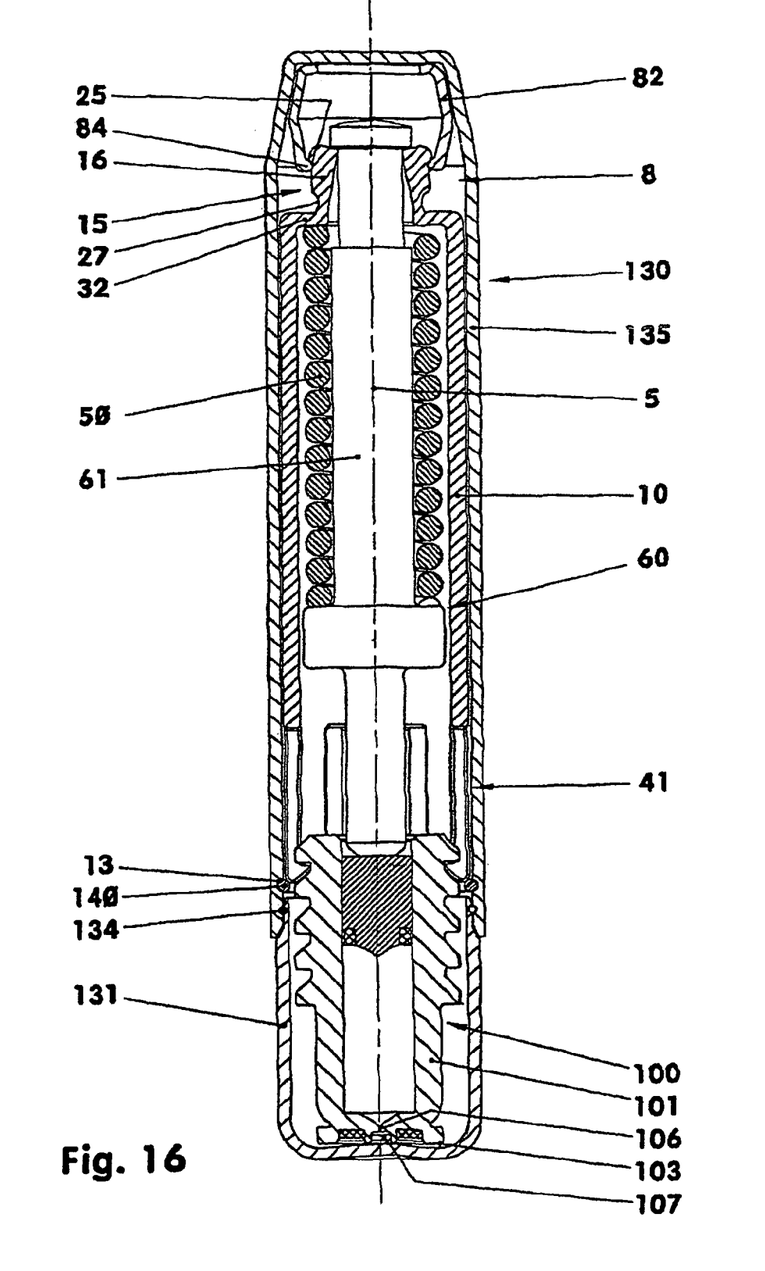
FIG. 16 shows a disposable injector according to FIG. 5, but with a completely closed housing.
Figure 17:
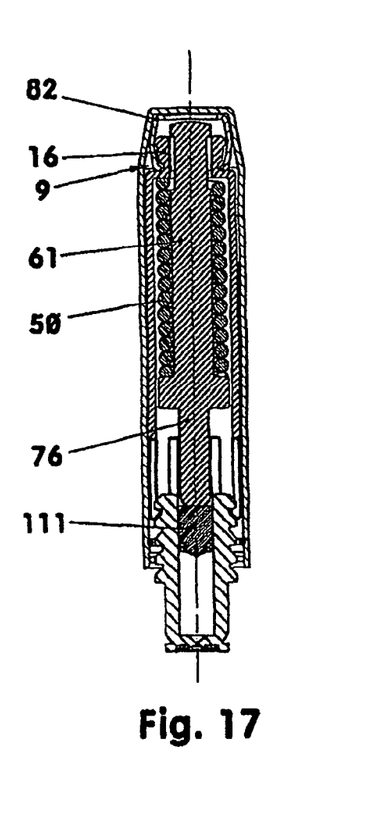
FIG. 17 is as per FIG. 16, but released and actuated.
Figures 18, 19:
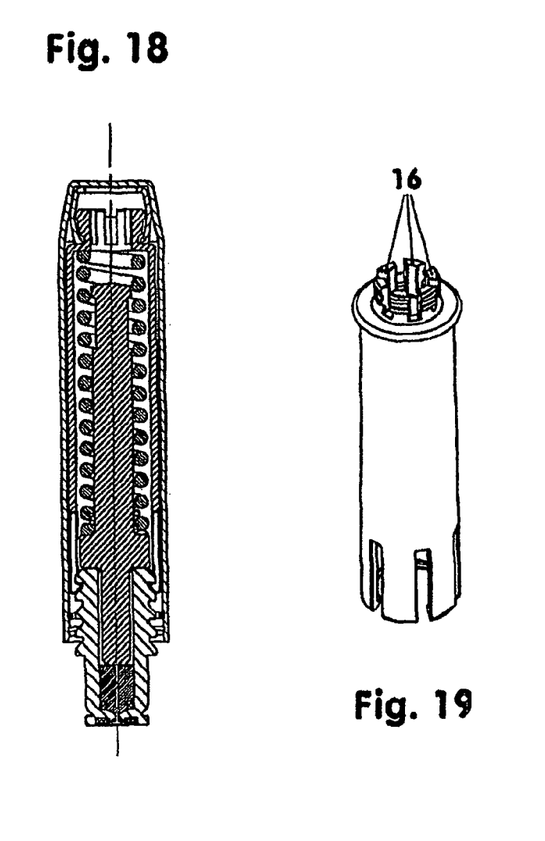
FIG. 18 is as per FIG. 17, but after the ejection of medicament.
FIG. 19 shows the perspective plan view of the housing of the disposable injector according to FIG. 16.

If, after removal of the securing element (95) and pulling off of the protective film (120), see FIG. 15, the cap (82) is pressed downwards, the supporting web (86) slides into the offset region (27) of the locking elements (16). The locking elements (16) spring apart at least to an extent such that the tension bar (61) is released, see FIG. 12. The spring element (50) then pushes the piston-actuating ram (76) downwards, see FIG. 13. The injection operation is at an end when the medicament is dispensed via the cylinder/piston unit (100).

FIGS. 16 to 20 show a variant of a disposal injector which is inserted completely into a surrounding housing (130) which is sealed in a sterile manner. The surrounding housing (130) comprises a large upper part (135) and a smaller lower part (131). It surrounds the disposable injector in a protective manner.

Figure 20:
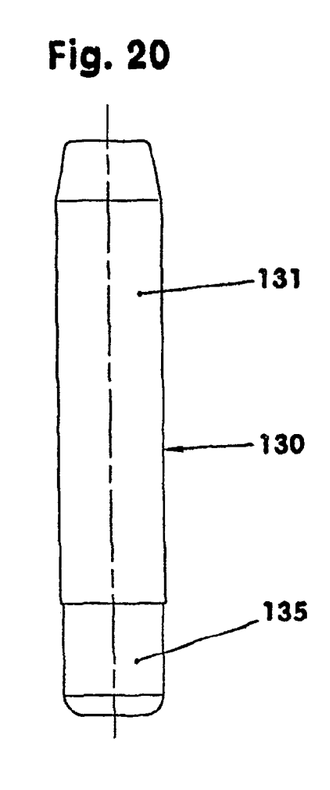
FIG. 20 shows a side view of the disposable injector according to FIG. 16, but before use.

The upper part (135) is illustrated here with a smooth, for the most part cylindrical outer surface, see FIG. 20. If appropriate, this outer surface may also be equipped with a slip-resistant structure and/or with gripping shells.

The two parts (131) and (135) are connected to each other in an insertable manner. For this purpose, according to FIG. 16, the lower part (131) is inserted in the upper part (135). In addition, the parts (131, 135) overlap in some regions. In the overlapping zone, for example, a sealing ring (134) which seals in a sterile manner sits in a protected manner. For example, it is adhesively bonded to the lower part (131).

In the region of the recess (107), the inner base of the lower part (131) is coated, for example, with a rubber coating which, when the surrounding housing (130) is installed, nests elastically against the base (103) of the cylinder/piston unit (100) such that it forms a sterile seal at least in the central base region.

The disposable injector parts (10, 50, 60 and 100) known from FIGS. 5 to 10 sit in the surrounding housing (130). A cap-shaped triggering element (82) which, at least as regards its upper design, is fitted in the upper part (135) sits on the locking elements (16).

The housing (10) is fixed in the upper part (135) by means of a, for example, toroidal securing ring (140). The securing ring (140) is embedded in a housing groove (13).

To assemble said disposable injector, the triggering element (82) is pulled over the locking elements (16). In the process, the border (84) is located in the offset region (27), see FIG. 18. In a further step, the spring element (50) is placed onto the piston-actuating ram (60) and is pushed by the latter from below into the housing (10), for example until the spring element (50) is set, see FIG. 17. The triggering element (82) is now pulled upwards such that the border (84) latches into the notch (25), see also FIG. 6. The piston-actuating ram (60) is now in its locking position (8).

In a further step, the filled cylinder/piston unit (100) is latched in the housing (10). The housing (10) together with the previously fitted parts (50, 60 and 100) is subsequently pushed into the upper part (135) and secured by means of the securing ring (140) against dropping out. Assembly is ended by the lower part (131) being inserted into the upper part (135).

In the event of use, the disposable injector is released by the lower part (131) being pulled off. In order for it to be triggered, the injector is held at the upper part (135) and, with the nozzle bore (106) in front, is pressed against the portion of skin at which the injection is desired. The pressure against the skin causes the upper part (135) to push the triggering element (82) against the base (32) of the housing (10) the injection operation begins. After rapid emptying of the cylinder (100), the operation is finished.

With the exception of the spring elements (50, 29) and the piston plate (116), all of the parts of the previously described disposable injectors are manufactured from plastics materials or material similar to plastic or rubber.

LIST OF REFERENCE NUMBERS

1 Injection solution; medicament
5 Centre line of the disposable injector
8 Locking position
9 Release position
10 Housing, single-part
11 Housing interior
12 Housing end side, bottom
13 Housing groove
14 Annular groove
15 Triggering region
16 Locking elements
17 Lever arm, short
18 Lever arm, long
19 Supporting elements
21 Bearing region
22 Bearing surface, top, inside
23 Bearing surface, lateral, outside
24 Retaining region
25 Notch
27 Offset region
28 Offset notch, offset contour
29 Helical compression spring
31 Casing region
32 Base, intermediate base
34 Opening, bore, recess
35 Housing collar
39 Housing surround
41 Fixing region for the cylinder/piston unit
42 Spring hook
43 Hook tip
44 Bevel
46 clamping sleeve
47 Grooved profile
50 Spring element, helical compression spring, spring energy reservoir
60 Piston-actuating ram
61 Tension bar
62 Guide pin
63 Supporting surface, toroidal partial surface
64 Transition surface
73 Ram plate
76 Piston slide
80 Triggering unit
82 Triggering element
83 Base, grooved
84 Border, inwardly curved
85 Outer border
86 Supporting webs
87 Engaging-around border
88 Web, encircling
89 Tube section
95 Securing element
96 Disc, plate-like
97 Locking pin
98 Handle
100 Cylinder/piston unit
101 Cylinder
102 Latching ribs, outside; outside grooving
103 End surface
106 Bore, nozzle
107 Recess in the end surface
108 Elevation
111 Piston
112 Annular groove
114 Sealing ring, seal
116 Metal plate, magnetic or magnetizable
120 Protective film, adhesive seal
130 Surrounding housing
131 Lower part, securing element
132 Bore
133 Border
134 Seal, sterile
135 Upper part, securing element
137 Border
138 Surrounds
139 Film hinge
140 Securing ring, toroidal

What is claimed is:
1. A disposable injector comprising:
 a housing (10) in which is arranged at least one helical compression spring (50),
 a cylinder/piston unit (100) including a piston (111) and a cylinder (101) having an interior for operatively receiving and being filled and containing at least temporarily an active substance,
 a spring-loaded piston-actuating ram (60) and at least one triggering unit (80) in operative arrangement therewith, the spring-loaded piston-actuating ram (60) includes proximate a central region thereof a ram plate (73) and the spring-loaded piston-actuating ram (60) includes above the ram plate (73) a non-transversely moveable tension bar (61), the at least one helical compression spring (50) includes at least one pre-loaded spring element, and at least part of the piston-actuating ram (60) is operatively arranged between the at least one triggering unit (80) and the piston (111) of the cylinder/piston unit (100), the at least one helical compression spring (50) is arranged coaxially with a substantial portion of the non-transversely moveable tension bar (61)

the non-transversely movable tension bar (61) has a throat-like constriction having at least one supporting surface (63) in the region of the upper end of the non-transversely moveable tension bar (61), the housing (10) includes an elevated intermediate base (32), the elevated intermediate base (32) has as monolithic portions thereof flexurally elastic elements (16) which operatively extend from the elevated intermediate base (32), the flexurally elastic elements (16) have a locking position (8), a triggering element (82) operatively secures the flexurally elastic elements (16) in the locking position (8), the flexurally elastic elements (16) each having a bearing region (21) of predetermined maximum outside diameter having an upper bearing surface (22) operatively supporting and contacting the supporting surface (63) of the non-transversely moveable tension bar (61) in the locking position (8), the flexurally elastic elements (16) each having below the bearing region (21) a retaining region (24) having a predetermined maximum outside diameter smaller than the maximum outside diameter of the bearing region (21) and having a lateral bearing surface (23) for contacting a web (86) or a lower supporting border (84) of the triggering element (82) in the locking position (8), the flexurally elastic elements (16) each having below and adjoining the retaining region (24) an offset region (27) having a maximum outside diameter a predetermined amount smaller than the maximum outside diameter of the retaining region (24) for permitting lateral movement of each of the flexurally elastic elements by release thereof by the web (86) or lower supporting border (24) upon operative movement of the triggering element (82), the flexurally elastic elements (16) have a release position (9), the operative movement of the triggering element (82) operatively releases the upper bearing surface (22) of each of the flexurally elastic elements (16) from contact with the at least one supporting surface (63) of the non-transversely moveable tension bar (61) operatively releasing the non-transversely moveable tension bar (61) for causing the piston (111) to force the active substance from the interior of the cylinder (101) while simultaneously the web (86) or lower supporting border (84) of the triggering element (82) allows lateral movement of each of the flexurally elastic elements (16) in the offset region (27) thereby releasing the non-transversely moveable tension bar (61), and, the at least one helical compression spring (50) is positioned in a pre-loaded state between the ram plate (73) and the elevated base (32) of the housing (10).

2. The disposable injector according to claim 1, wherein the upper bearing surface (22) of an individual flexurally elastic element (16) is operatively positioned closer to the housing centre line (5) in the elastically deformed locking position (8) than in the un-deformed release position (9).

3. The disposable injector according to claim 1, wherein the at least one supporting surface (63) of the non-transversely moveable tension bar (61) is the inner surface of a toroidal casing or of a frustoconical casing surface.

4. The disposable injector according to claim 3, wherein the upper bearing surface (22) of each of the flexurally elastic elements (16) has a continuously curved contour that is part of a toroidal outer surface, the at least one supporting surface (63) of the non-transversely moveable tension bar (61) and the upper bearing surface (22) of the flexurally elastic elements (16) have about the same circular cross-sectional radius and the same annular radii, whereby particularly large contact surfaces between the non-transversely moveable tension bar (61) and flexurally elastic elements (16) are provided.

5. The disposable injector according to claim 1, further including a securing element (95, 135) operatively securing the non-transversely moveable tension bar (61) in the locking position (8), the securing element (95, 135) operatively arranged on the housing (10, 130) or on the triggering unit (80).

6. The disposable injector according to claim 1, wherein the cylinder (101) has a base in the center of the interior or cylindrical bore of the cylinder (101) having a contour at least approximately matching the contour of a front or a lower end of the piston (111).

7. The disposable injector according to claim 6, wherein the base of the cylinder (101) proximate the centre of the interior or cylindrical bore has a short cylindrical nozzle-like bore (106).

8. The disposable injector according to claim 1, further comprising an adhesive seal (120) removably affixed to a lower end side of the cylinder/piston unit (100) for closing the lower end side of the cylinder/piston unit (100) in a sterile manner.

9. The disposable injector according to claim 1, wherein the upper bearing surface (22) of each of the flexurally elastic elements (16) further include ceramic armouring affixed to the upper bearing surface (22).

\* \* \* \* \*